US007700752B2

(12) United States Patent
Szabo et al.

(10) Patent No.: US 7,700,752 B2
(45) Date of Patent: Apr. 20, 2010

(54) PROCESS FOR CONSTRUCTING STRAIN HAVING COMPACTIN HYDROXYLATION ABILITY

(75) Inventors: Lorand Szabo, Godollo (HU); Ronen Tchelet, Pardesia (IL)

(73) Assignee: Teva Gyogyszergyar Zartkoruen Mukodo Reszvenytarsasag, Debrecen (HU)

( * ) Notice: Subject to any disclaimer, the term of this patent is extended or adjusted under 35 U.S.C. 154(b) by 327 days.

(21) Appl. No.: 11/827,162

(22) Filed: Jul. 10, 2007

(65) Prior Publication Data

US 2009/0004695 A1 Jan. 1, 2009

Related U.S. Application Data

(62) Division of application No. 11/295,142, filed on Dec. 5, 2005.

(60) Provisional application No. 60/633,011, filed on Dec. 3, 2004.

(51) Int. Cl.
*C07H 21/04* (2006.01)
*C12N 9/02* (2006.01)
*C12P 21/06* (2006.01)
*C12N 15/70* (2006.01)
*C12N 1/20* (2006.01)

(52) U.S. Cl. .................. 536/23.2; 435/189; 435/69.1; 435/252.33; 435/252.35; 435/320.1; 435/135

(58) Field of Classification Search .................. None
See application file for complete search history.

(56) References Cited

U.S. PATENT DOCUMENTS

| 4,537,859 | A | 8/1985 | Terahara et al. |
| 5,179,013 | A | 1/1993 | Matsuoka et al. |
| 5,830,695 | A | 11/1998 | Serizawa et al. |
| 6,566,120 | B2 | 5/2003 | Demain et al. |
| 6,750,366 | B2 | 6/2004 | Jekkel et al. |

FOREIGN PATENT DOCUMENTS

| CA | 1150170 | 7/1983 |
| CA | 1186647 | 5/1985 |
| EP | 0 605 230 | 8/1997 |
| EP | 1 500 704 | 1/2005 |
| JP | 58-010572 | 1/1983 |
| JP | 6-070780 | 3/1994 |
| JP | 11-235174 | 8/1999 |
| WO | WO 94/29292 | 12/1994 |
| WO | WO 97/06128 | 2/1997 |
| WO | WO 00/46175 | 8/2000 |
| WO | WO 03/087381 | 10/2003 |

OTHER PUBLICATIONS

Chica et al. Semi-rational approaches to engineering enzyme activity: combining the benefits of directed evolution and rational design, Curr Opin Biotechnol. Aug. 2005;16(4):378-84. Review.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Whisstock et al. Quaterly Reviews of Biophysics, 2003, "Prediction of protein function from protein sequence and structure", 36(3): 307-340.*
D.P. O'Keefe, et al. "Ferredoxins from Two Sulfonylurea Herbicide Monooxygenase Systems in *Streptomyces griseolus*" *Biochemistry*, (1991), vol. 30, pp. 447-455.
P.A. Harder, et al. "Isolation and Characterization of *Streptomyces griseolus* Deletion Mutants Affected by Cytochrome P-450-Mediated Herbicide Metabolism" *Mol. Gen. Genet.* (1991), vol. 227, pp. 238-244.
C.A. Omer, et al. "Genes for Two Herbicide-Inducible Cytochromes P-450 from *Streptomyces griseolus*" *Journal of Bacteriology*, (1990), vol. 172, No. 6, pp. 3335-3345.
I. Watanabe, et al. "Molecular Approaches for Production of Pravastatin, a HMG-COA Reductase Inhibitor: Transcriptional Regulation of the Cytochrome P450$_{sca}$ gene from *Streptomyces carbophilus* by ML-236B Sodium Salt and Phenobarbitual" *Gene*, (1998), vol. 210, pp. 109-116.
N. Serizawa, et al. "Microbial Hydroxylation of ML-236B (Compactin) Studies on Microorganisms Capable of 3β-Hydroxylation of ML-236B" *The Journal of Antibiotics*, (1983), vol. 36, pp. 887-891.
N. Serizawa, et al. "6α-Hydroxy-Iso-ML-2368 (6α-Hydroxy-Iso-Compactin) and ML-236A, Microbial Transformation Products of ML-236B" *The Journal of Antibiotics*, (1983), vol. 36, pp. 918-920.
N. Serizawa, et al. "Microbial Hydroxylation of ML-236B (Compactin) and Monacolin K (MB-530B)" *The Journal of Antibiotics*, (1983), vol. 36, pp. 604-607.
N. Serizawa, et al. "A Two Component-Type Cytochrome P-450 Monooxygenase system . . . ML-236B to Pravastatin, A Tissue-Selective Inhibitor of 3-Hydroxy-3-Methylglutaryl Coenzyme A Reductase" *Biochimica et Biophysica Acta*, (1991), vol. 1084, pp. 35-40.
Y. Tsujita, et al. "CS-514, A Competitive Inhibitor of 3-Hydroxy-3-Methylglutaryl Coenzyme A Reductase: Tissue-Selective Inhibition of Sterol Synthesis and Hypolipidemic Effect on Various Animal Species" *Biochimica et Biophysica Acta*, (1986), vol. 877, pp. 50-60.

(Continued)

*Primary Examiner*—Richard Hutson
*Assistant Examiner*—Iqbal H Chowdhury
(74) *Attorney, Agent, or Firm*—Merchant & Gould PC

(57) ABSTRACT

The present invention is directed to methods and compositions for microbial based production of pravastatin. The compositions of the invention include novel strains of microorganisms that are capable of efficiently hydroxylating compactin (ML-236 B) resulting in production of pravastatin. In particular, the microorganisms of the invention are genetically engineered to express both cytochrome P-450 and the fdxshe or fdxshe-like protein. The invention further relates to the use of such microorganisms in processes designed for production of pravastatin for use in treatment of disease such as hypercholesterolemia and hyperlipidemia.

9 Claims, 4 Drawing Sheets

OTHER PUBLICATIONS

M. Arai, et al. "Pravastatin Sodium (CS-514), A Novel Cholesterol-Lowering Agent Which Inhibits HMG-CoA Reductase" *Sankyo Kenkyusho Nempo*, (1988), vol. 40, pp. 1-38.

T. Koga, et al. "Tissue-selective Inhibition of Cholesterol Synthesis In Vivo by Pravastatin Sodium, A 3-Hydroxy-3-Methylglutaryl Coenzyme A Reductase Inhibitor" *Biochimica et Biophysica Acta*, (1990), vol. 1045, pp. 115-120.

T. Matsuoka, et al. "Purification and Characterization of Cytochrome P-$450_{sca}$ from *Streptomyces carbophilus*" *Eur. J. Biochem.*, (1989), vol. 184, pp. 707-713.

I. Watanabe, et al. "Cloning, Characterization and Expression . . . Cytochrome P-$450_{sca}$ from *Streptomyces carbophilus* Involved in Production of Pravastatin, a Specific HMG-CoA Reductase Inhibitor" *Gene*, (1995), vol. 163, pp. 81-85.

* cited by examiner

FIGURE 1.: SEQ. ID NOS.: 1 AND 2

```
1    CCGAGCGGAA AGGAGGACCC ATGCGGGTCT CAGCGGACCG GGACGTCTGT GTCGGCGCCG GCCTGTGCGC GCTGACCGCG CCCGACGTCT
     GGCTCGCCTT TCCTCCTGGG TACGCCCAGA GTCGCCTGGC CCTGCAGACA CAGCCGCGGC CGGACACGCG CGACTGGCGC GGGCTGCAGA
     >>........................................fdxshe......................................>
                MetArgVal SerAlaAsp ArgAspValCys ValGlyAla GlyLeuCys AlaLeuThrAla ProAspVal 91   TTGACCAGGA CGACGACGGC CTTGTTGACG TGGTCACCCC CGATCCCGGC CAGGCGCAGC AGGCCGCGGC CCGCCAGGCC GGCAACCTCT
     AACTGGTCCT GCTGCTGCCG GAACAACTGC ACCAGTGGGG GCTAGGGCCG GTCCGCGTCG TCCGGCGCCG GGCGGTCCGG CCGTTGGAGA
     >........................................fdxshe.......................................>
     PheAspGln AspAspAspGly LeuValAsp ValValThr ProAspProGly GlnAlaGln GlnAlaAla AlaArgGlnAla GlyAsnLeu 181  GTCCGGTCGG GGCGGTCCCG ATCACCGAAT GANGCCGACCG TCCCGCGGCC
     CAGGCAGCC CCGCCAGGCG TAGTGGCTTA CTNCGCTGGC AGGGCGCCGG
     >........................................fdxshe......>>
     CysProSer GlyAlaValArg IleThrGlu ---
```

S.l: *Streptomyces lividans*
S.h: *Streptomyces helvaticus*
P450: strain containing the plasmid with the cytochrome P450she gene
P450+trx: strain containing the plasmid with the cytochrome P450she + fdxshe gene
100 ul, 500 ul and 1000 ul: amount of 40 mg/ml compactin solution added to 50 ml of main fermentation medium.

FIGURE 4.
*Original theory (Matsuaka et al, 1989)* Novel two component system
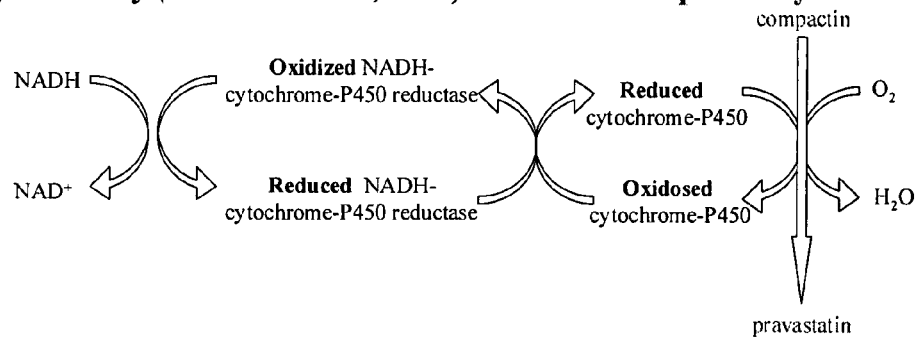
*New theory:* common three component system
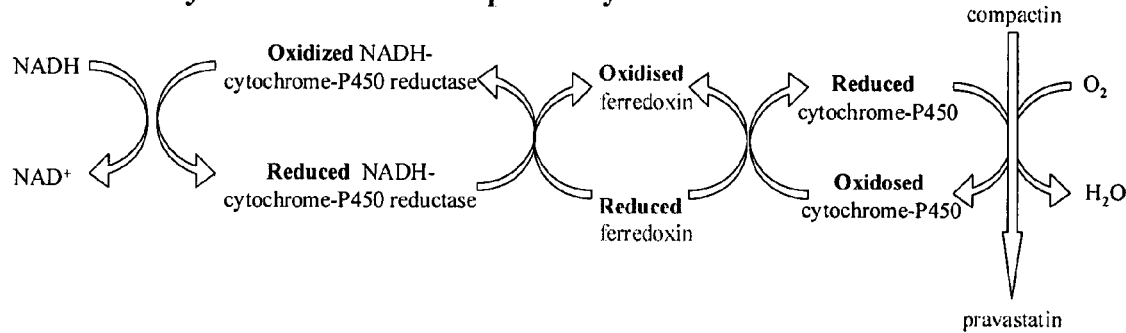

PROCESS FOR CONSTRUCTING STRAIN HAVING COMPACTIN HYDROXYLATION ABILITY

RELATED APPLICATIONS

This application is a divisional application of U.S. application Ser. No. 11/295,142, filed Dec. 5, 2005 which claims the benefit of U.S. provisional application No. 60/633,011, filed Dec. 3, 2004, hereby incorporated by reference.

FIELD OF THE INVENTION

The present invention relates to a new protein, fdxshe or fdxshe-like protein, associated with the gene encoding a P-450 cytochrome, and necessary for its activity. The present invention is directed to methods and compositions for microbial based production of pravastatin. The compositions of the invention include vectors containing this gene, the use of such vectors in expression systems, and novel strains of microorganisms that are capable of efficiently hydroxylating compactin (ML-236 B) resulting in production of pravastatin. In particular, the microorganisms of the invention are genetically engineered to express both cytochrome P-450 and the newly discovered fdxshe or a fdxshe-like protein. The invention further relates to the use of such microorganisms in processes designed for production of pravastatin for use in treatment of diseases such as hypercholesterolemia and hyperlipidemia.

BACKGROUND OF THE INVENTION

Pravastatin is an inhibitor of HMG-CoA reductase (3-hydroxy-3-methylglutaryl coenzyme A reductase), a key enzyme in cholesterol biosynthesis. This enzyme significantly reduces plasma cholesterol and lipid levels and is thereby of great pharmacological importance in the therapy of hypercholesterolemia and hyperlipidemia. [Serizawa et al., J. Antibiot., 36: 887-891 (1983); Serizawa et al., J. Antibiot., 36: 918-920 (1983); Serizawa et al., J. Antibiot., 36: 604-607 (1983); Tsujita et al., Biochim. Biophys. Acta, 877: 50-60 (1986); Arai et al., Ann. Rep. Sankyo Res. Lab., 40:1-38 (1988); and Koga et al., Biochim. Biophys. Acta, 1045: 115-120 (1990).]

Pravastatin is obtained by microbial hydroxylation of sodium ML-236B (compactin), a substance produced by a filamentous fungus, *Penicillium citrinum*. This hydroxylation can be effected to differing degrees by many different genera of fungi, such as *Mucor Rhizopus, Syncephalastrum, Cunninghamella, Mortierella* and bacteria such as *Nocardia, Actinomadura* and *Streptomyces* as described in various patents. [U.S. Pat. Nos. 5,179,013; 4,448,979; 4,346,227; 4,537,859; 6,566,120; 6,750,366; Canadian patent Nos. 1,150,170; 1,186,647; Japanese Patent No. 58-10572; and European Patent No. 0605230]

The hydroxylation takes place at the 6-position of ML-236B, catalyzed by a Cytochrome P-450$_{sca}$ monooxygenase system, found in *Streptomyces carbophilus*. [Matsuoka et al., Eur. J. Biochem., 184: 707-713 (1989); and Serizawa, et al., Biochimica et Biophysica Acta, 1084: 35-40 (1991).] Cytochrome P-450$_{sca}$ was characterized as occurring in three forms: P-450$_{sca-1}$, P-450$_{sca-2}$, and P-450$_{sca-3}$, which according to U.S. Pat. No. 5,179,013, are suitable for use in hydroxylation processes.

Serizawa et al. cloned the DNA encoding P-450$_{sca-2}$ from *Streptomyces carbophilus*. [Japanese Patent Kokai No. 6-70780; and Watanabe et al., Gene, 163: 81-85 (1995).] The gene has an open reading frame of 1233 bp, encoding a 410 amino acid protein. [Watanabe et al., Gene, 163: 81-85 (1995).] A 2.8 kb DNA insert, along with a 1 kbp portion of the 5'-noncoding region of the P-450$_{sca-2}$ gene, was cloned into a multicopy plasmid, pIJ702, and used to transform *Streptomyces lividans* TK21. The transformed *Streptomyces lividans* TK21 converted ML-236B to pravastatin even faster than *S. carbophilus*. See, Watanabe, I. et al., Gene 163:81-85 (1995).

Watanabe et al. disclosed that the expression of P-450$_{sca}$ is subject to substrate induction of transcription, that is, ML-236B and phenobarbital were found to enhance the expression of P-450 by as much as 30-fold. This was established by Northern blotting, which found no transcription in the absence of ML-236B, but which found three transcripts when ML-236B was present. The levels of transcription increased over a period of six hours to a maximum rate when substrate was present. The DNA sequence of the 5' region was published, which coded a regulator like protein and the promoter sequence. [Watanabe et al., Gene 210, 109-116 (1998).]

A 1 kbp length of the 5'-noncoding region of the gene encoding cytochrome P-450sca-2 in the *Streptomyces carbophilus* has transcription promoter activity, which is substrate inducible. When the 1 kbp region was shortened, the transcription promoter allowed significant expression of the protein in a suitable expression system without having to be induced. [U.S. Pat. No. 5,830,695.]

Serizawa and Matsuoka purified a NADH-cytochrome-P-450-reductase from *S. carbophilus*. They used purified P-450$_{sca}$ protein to demonstrate in vitro hydroxylation activity in the presence of the purified flavoprotein (NADH-cytochrome-P-450-reductase), NADH and O$_2$. They disclosed that P-450$_{sca}$ and NADH-cytochrome-P-450 reductase reconstituted the hydroxylation activity in vitro and did not obtain any evidence for existence of iron-sulfur protein in *S. carbophilus*. Based on these findings, Serizawa and Matsuoka classified the P-450$_{sca}$ cytochrome system as a two component system similar to those found in microsomal cytochrome systems of eukaryotes, which do not require iron-sulfur proteins. [Serizawa and Matsuoka, Biochem et Biophysica Acta, 1084: 35-40 (1991).]

The present invention is based on the discovery that the gene encoding fdxshe or a fdxshe-like protein is located downstream from the cytochrome P-450 gene and is necessary for the function of the P-450$_{sca}$ cytochrome. Thus, the P-450$_{sca}$ cytochrome system is a three component system, in contradistinction to the proposed two component system proposed by Serizawa and Matsuoka, as described in FIG. 4.

SUMMARY OF THE INVENTION

It is an objective of the invention to provide an effective and efficient method for converting compactin to pravastatin.

It is another objective of the invention to use co-expression of cytochrome P-450 and the ferredoxin or the ferredoxin-like protein to convert compactin to pravastatin.

The invention encompasses novel microorganisms capable of hydroxylating compactin (ML-236B) and thereby producing pravastatin. The microorganisms of the invention are genetically engineered to express both cytochrome P-450 and the ferredoxin or the ferredoxin-like protein. The invention is based on the discovery that co-expression of cytochrome P-450, in conjunction with the ferredoxin or the ferredoxin-like protein, results in production of pravastatin.

The invention further encompasses processes of constructing a genetically modified microorganism having compactin hydroxylation ability comprising transforming a host cell with one or more plasmid constructs comprising a promoter and nucleic acid sequences encoding cytochrome P-450 and the ferredoxin or the ferredoxin-like protein.

Another embodiment of the invention encompasses processes for producing pravastatin using fermentation techniques known in the art, comprising culturing the genetically modified microorganism of the invention in a medium containing ML-236B under conditions wherein the cytochrome P-450 and the ferredoxin or the ferredoxin-like protein are expressed resulting in catalytic conversion of ML-236B to pravastatin.

In yet another aspect of the invention, the process may further comprise recovering the pravastatin from the culture medium and its use in treatment of disorders related to cholesterol biosynthesis such as hypercholesterolemia and hyperlipidemia.

The present invention also encompasses a novel nucleic acid molecule encoding fdxshe.

The present invention also encompasses the vector containing the said nucleic acid molecule.

The present invention also encompasses a novel protein encoded by fdxshe and methods for its production using the said vector.

The above and other objectives, features and advantages of the present invention will be better understood from the following specification.

BRIEF DESCRIPTION OF THE DRAWINGS

FIG. 1 illustrates a nucleic acid (upper strand—SEQ ID NO: 1; lower strand—SEQ ID NO: 3) and amino acid (SEQ ID NO: 2) sequence of fdxshe.

FIG. 4 illustrates the two component model of compactin hydroxylation without ferredoxin and the novel three component model of compactin hydroxylation of the present invention with ferredoxin.

DETAILED DESCRIPTION OF THE INVENTION

Figure 2:
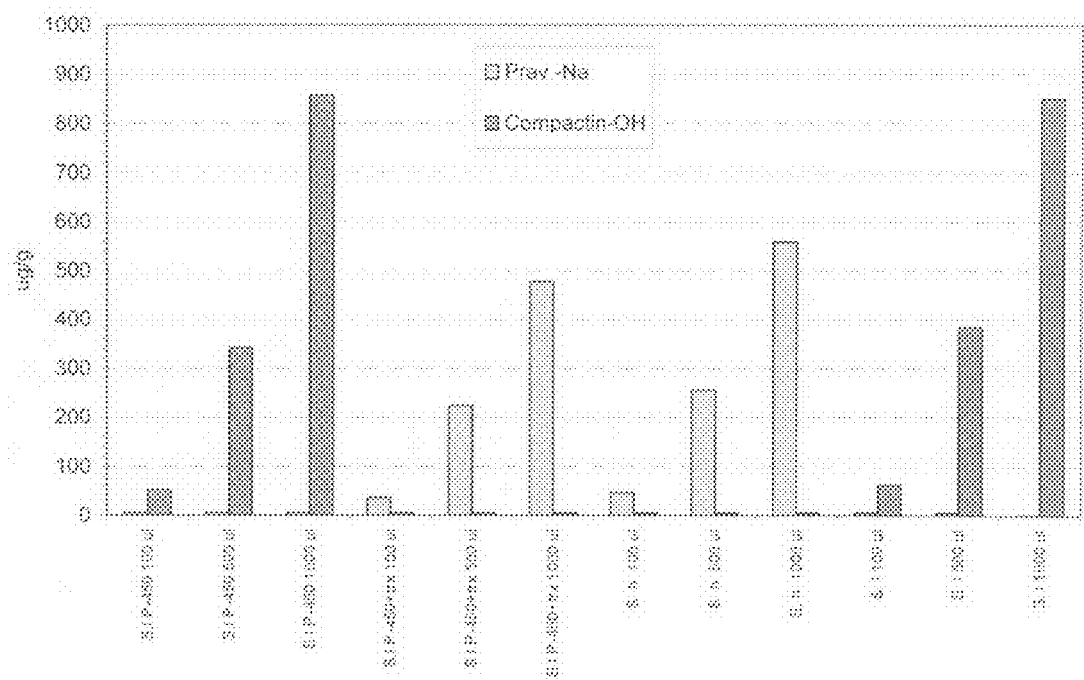
FIG. 2 illustrates pravastatin and compactin quantitative determination: Bars show remaining soluble form of compactin (compactin-OH) and produced pravastatin after overnight incubation by *S. lividans* strains harboring different plasmid constructs or by *S. helvaticus*.
Figure 3:
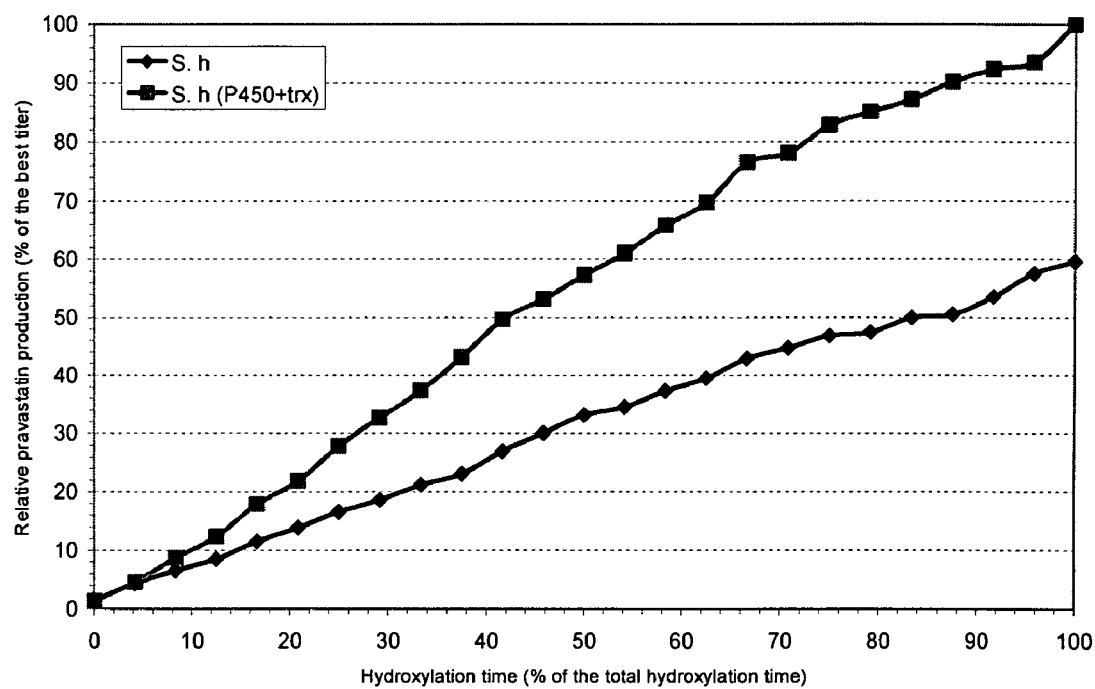
FIG. 3 illustrates the pravastatin production rate of the *S. helvaticus* colonies with and without the pWHM-cytP450she-fdxshe plasmid.

Described herein is the discovery that co-expression of cytochrome P-450 and the ferredoxin or a ferredoxin-like protein in genetically engineered microorganisms, results in hydroxylation of ML-236B (compactin) to form pravastatin. The present invention, described in detail below, is directed to such microorganisms as well as their use in production of pravastatin for use in treatment of disorders related to cholesterol biosynthesis. Such disorders include, but are not limited to, hypercholesterolemia or hyperlipidemia.

As used herein, the ferredoxin or a ferredoxin-like protein is the fdxshe gene of *Streptomyces helvaticus*. The nucleic acid molecule has been found to correspond to a 188 base pair sequence [See SEQ ID NO: 1, FIG. 1], located downstream from the cytochrome P-450 open reading frames.

As used herein, ML-236B includes ML-236 and salts thereof. In a preferred embodiment the ML-236 is sodium ML-236. As used herein, pravastatin refers to pravastatin, and salts thereof. In a preferred embodiment, the pravastatin is pravastatin sodium.

Preferably, the ML-236B (compactin) is provided by providing, e.g., a microorganism, e.g. a fungus or bacterium, that produces compactin, or a cell free extract of a microorganism that produces compactin, or a cell free culture media from a pregrown culture of a microorganism that produces compactin, or a solution comprising compactin, or semi-purified compactin, or substantially purified compactin or salts thereof. The culturing being under conditions wherein cytochrome P-450 and ferredoxin or a ferredoxin like protein are expressed, thereby allowing the ML-236B to be converted to pravastatin by catalytic action of the cytochrome P-450 and then recovering the pravastatin from the culture.

The present invention encompasses microorganisms transformed with one or more expression vectors capable of encoding cytochrome P-450 and the ferredoxin or a ferredoxin-like protein. The choice of expression vectors to be used in the practice of the invention will depend on the type of microorganism being transformed. For example, it is essential that the expression vector sequences required for replication, transcriptional regulation, translational control, etc. are compatible with the microorganism chosen for transformation. Bacterial expression vectors include, but are not limited to, those based on bacteriophage DNA or plasmid DNA and include those that are appropriate for transformation of such prokaryotes as actinomycetes, *Escherichia coli* and *Bacillus subtilis*, to name a few. In a preferred embodiment of the invention, actinomycete compatible expression vectors such as plasmid pWHM-3 are used.

While expression vectors of the present invention need have no further features than those required for expression in a given host, it will be appreciated that built-in selection criteria can be useful. Such criteria include those whereby the plasmid confers on the host such properties as selectivity of expression and transformation, so that the phenotype is modified. Suitable selective markers, i.e. those conferring a particular phenotype on the host, include such drug-resistance marker genes as those conferring resistance to thiostreptone, ampicillin, tetracycline, or chloramphenicol; however, it will be appreciated that many other selective markers may be used.

Methods that are well known to those skilled in the art can be used to construct expression vectors containing cytochrome P-450 coding sequences and/or the ferredoxin or a ferredoxin-like protein coding sequences and appropriate transcriptional and translational control sequences. To construct the expression vectors, DNA fragments comprising nucleic acids encoding cytochrome P-450 and the ferredoxin or a ferredoxin-like protein are inserted into an expression vector together with the appropriate transcriptional and translational control sequences. Such transcriptional control sequences include, for example, promoter sequences. Such translational control sequences include, for example, ribosome binding sequences. In an embodiment of the invention, the cytochrome P-450 and/or encoding sequences and the ferredoxin or a ferredoxin-like protein encoding sequences are inserted into a single vector. Alternatively, the encoding sequences may be inserted into separate vectors which are then co-transformed into host cells. Methods commonly known in the art of recombinant DNA technology which can be used for cloning of nucleic acid molecules into expression vectors are described in Ausubel et al. (eds.), 1993, Current Protocols in Molecular Biology, John Wiley & Sons, NY: and Kriegler, 1990, Gene Transfer and Expression, A Laboratory Manual, Stockton Press, NY.

With respect to sequences encoding cytochrome P-450, such sequences may be derived from a variety of different microorganisms using a variety of different methods known to those skilled in the art. For example, a genomic DNA library can be screened using a labeled cytochrome P-450 probe. For guidance on hybridization conditions see, for example, Ausubel et al., supra. Further, cytochrome P-450 nucleic acid sequences may be derived by performing PCR using two oligonucleotide primers designed on the basis of known cytochrome P-450 nucleotide sequences disclosed herein. In a preferred embodiment of the invention, the cytochrome P-450 encoding sequences are isolated from strains that cannot be clearly differentiated from actinomycete, preferably strains that cannot be clearly differentiated from *Streptomyces*, more preferably strains that cannot be clearly differentiated from *S. carbophilus* or *S. helvaticus*. See, Watanabe et al., Gene, 163: 81-85 (1995).

With respect to ferredoxin or ferredoxin like protein coding sequences, such sequences may also be derived from a variety of different microorganisms using the methods described above for isolation of cytochrome P-450 encoding sequences. Several forms of ferredoxin such as 3Fe-4S of *S. griseolus*, PimF protein of *S. natalensis*, and RimH protein of *S. diastaticus* are known and may be used in the construction of the expression vectors. In addition, the novel ferredoxin or ferredoxin like protein encoding sequence described below may be used in the construction of expression vectors.

The present invention provides a novel ferredoxin gene derived from *S. helvaticus*. The novel gene has been identified and cloned downstream from the cytochrome P-450 gene in *S. helvaticus* and is referred to as fdxshe. The cloned fdxshe gene of the present invention is 188 bp long and shows over 80% homology with the ferredoxin of *S. griseolus* SauC and over 70% homology with ferredoxin of *S. natalensis* (PimF) or *S. diastaticus* (RimH). The nucleotide sequence and deduced amino acid sequence of fdxshe is shown in FIG. 1. The fdxshe nucleotide sequences of the invention include: (a) the DNA sequences shown in FIG. 1; (b) a nucleotide sequences that encodes the amino acid sequence shown in FIG. 1; (c) any nucleotide sequence that (i) hybridizes to the nucleotide sequence set forth in (a) or (b) under stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I Green Publishing Associates, Inc., and John Wiley & sons, Inc., New York, at p. 2.10.3) and (ii) encodes a functionally equivalent gene product.

The invention also includes nucleic acid molecules that may encode or act as fdxshe antisense molecules, useful, for example, in fdxshe gene regulation (for and/or as antisense primers in amplification reactions of fdxshe gene nucleic acid sequences). The invention also encompasses nucleotide sequences that encode mutant fdxshe, peptide fragments of fdxshe, truncated fdxshe, and fdxshe fusion proteins.

The invention also encompasses (a) DNA vectors that contain any of the foregoing fdxshe sequences and/or their complements (e.g., antisense, RNAi); (b) DNA expression vectors that contain any of the foregoing fdxshe sequences operatively associated with a regulatory element that directs the expression of the fdxshe coding sequences; and (c) genetically engineered host cells that contain any of the foregoing fdxshe sequences operatively associated with a regulatory element that directs the expression of the fdxshe coding sequences in the host cell. As used herein, regulatory elements include, but are not limited to, inducible and non-inducible promoters, operators, and other elements known to those skilled in the art that drive and regulate gene expression.

FIG. 1 shows the nucleic acid sequence of the fdxshe gene as well as a corresponding deduced amino acid sequence of the fdxshe protein. The fdxshe amino acid sequences of the invention include the amino acid sequence shown in FIG. 1. The invention also encompasses proteins that are functionally equivalent to the fdxshe encoded by the nucleotide sequences described in FIG. 1, as judged by any of a number of criteria including but not limited to the ability to catalyze, in conjunction with cytochrome P-450, conversion of ML-236B to pravastatin. Such functionally equivalent fdxshe proteins include, but are not limited to, proteins having additions or substitutions of amino acid residues within the amino acid sequence encoded by the fdxshe nucleotide sequences described above, but which result in a silent change, thus producing a functionally equivalent gene product.

Expression of the sequences encoding the cytochrome P-450 and ferredoxin or ferredoxin like proteins can be modulated by any regulatory promoter known in the art to function in the particular microorganism of choice. Such promoters can be inducible or constitutive. It is generally preferred to use a promoter with significantly higher activity, rather than lower activity, so that maximum transcription can be achieved. Such promoters include, but are not limited to, the lac, tac, cat, xyl, ptipA, tsr, or pkg promoters.

In an embodiment of the invention, the promoter located immediately adjacent to and associated with a cytochrome P-4500RF of an actinomycete, preferably a *Streptomyces*, more preferably *S. carbophilus* or *S. helvaticus* may be used. The approximately 1 kilobase region 5' and adjacent to the P-450 ORF does not necessarily contain the entire promoter region for this gene and according to U.S. Pat. No. 5,830,695 ("the '695 patent") the DNA of the promoter region may be considerably shorter than about 1 Kb preferably greater than about 160 bp, more preferably greater than about 300 bp. The promoter of the present invention can vary as much as is desired from the original 5' promoter, provided that the resulting promoter still exhibits the requisite promoter activity. The '695 patent is hereby incorporated by reference to disclose the various sizes of promoters that may be utilized to express cytochrome P-450 and/or ferredoxin or ferredoxin like protein.

In addition, the following methods may be used to identify DNA sequences having promoter activity for insertion into the expression vectors of the invention. To identify, or test DNA sequences for transcriptional promoter activity (i) a recombinant expression vector is constructed, wherein DNA encoding a suitable protein is operatively ligated with the putative promoter DNA and inserted into a suitable vector, for example, the actinomycete plasmid pIJ702 or pWHM-3 [Katz, E., et al., (1983), J. Gen. Microbiol., 129, 2703-2714], and then (ii) a suitable host cell which allows the vector to stably replicate, for example, *Streptomyces lividans* when using the vectors pIJ702 or pWHM-3, are transformed with the vector.

Transformation can be carried out in accordance with Hopwood, et al., [c.f. Hopwood, D. A., et al., (1985), "Genetic Manipulation of *Streptomyces*: A Laboratory Manual", The John Innes Foundation, Norwich, UK] when the transformant is, for example, a streptomycete. It will be appreciated that the gene used to assay promoter activity should not usually be present or expressed in the host, prior to transformation.

Levels of transcription can be readily established by Northern blotting or RNA-PCR [Polymerase Chain Reaction, c.f. Innis, M. A., et al., (1990), "PCR PROTOCOLS", Academic Press, New York], for example. Levels of expression of the product may be established by determining the physiological activity of the protein produced. Thus, for example, a recombinant DNA vector may be prepared, wherein DNA encoding a protein with a given activity, such as an enzyme, is operatively connected, such as by ligation, to the 3'-terminal of the putative promoter. Levels of expression of the ORF connected to the putative promoter can then be assayed in a manner appropriate to the expression product.

It will be appreciated that methods for assaying expression products may be tailored specifically to the relevant products. For example, the putative promoter may be operatively linked to a drug-resistance gene, such as a chloramphenicol acetyl transferase gene [c.f. Gorman, C. M., et al., (1982), Mol. Cell. Biol., 2, 1044-1051], or to a luciferase gene [c.f. de Wet, J. R., et al., (1987), Mol. Cell. Biol., 7, 725-7371,], which can be detected by methods well known in the art. Other methods for assaying expression via the activity of the expression product may also be employed.

Another method for measuring expression, for example, is by way of recognizing the product using an appropriate antibody. Suitable measurement techniques include radioimmunoassay [c.f. Berson, R. S., et al., (1973), "Methods in Investigative and Diagnostic Endocrinology", Vol. 2A, 2B, North-Holland Publishing Co., Amsterdam], enzyme immunoassay [c.f. Engvall, E., (1980), Methods in Enzymology, 70(A), 419-439], Western blotting [c.f. Harlow, E., et al., (1988), "Antibodies—A Laboratory Manual", p. 471, Cold Spring Harbor Laboratory, New York] and immunoprecipitation [c.f. Kessler, S. W., et al., (1981), "Methods in Enzymology", 73(B), 442-459], depending on how it is desired to measure the interaction, and on whether the antibody or antigen is labeled in any way. In any event, it will be appreciated that the present discussion of these techniques is not exhaustive, and other methods will be readily apparent to those skilled in the art.

In instances where such an expression vector encodes the cytochrome P-450 and ferredoxin or ferredoxin like protein, and the plasmid is compatible with S. lividans, then the plasmid can be introduced into a strain of Streptomyces lividans not producing cytochrome P-450 or ferredoxin, and the transformant can then be cultured in the presence of ML-236B. The amount of pravastatin produced is then indicative of the level of expression of cytochrome P-450 and/or ferredoxin and ferredoxin-like promoters promoted by the putative promoter.

Once it has been established that DNA intended for use as a promoter of the present invention has the necessary activity as a promoter, then it may be employed to construct an expression vector for expression of cytochrome P-450 and/or ferredoxin or a ferredoxin like protein. As stated previously, cytochrome $P-450_{sca-2}$ is the preferred expression product, a suitable vector being pSCA1013-DELTA. (1013/428), said vector being isolatable from Streptomyces lividans TK-21.

Modifications to the sequences of the promoter, sequences encoding the ferredoxin or ferredoxin like proteins, i.e., fdx-she, or sequences encoding cytochrome P-450 may generally occur through the transformation procedure, or be made for convenience, such as to introduce a restriction site, for example. Thus, the present invention envisages promoters, ferredoxins, or cytochrome P-450, which may vary through deletions, inversions, insertions and substitutions. Preferably, the promoters, ferredoxins, and cytochrome P-450 of the invention share very substantial sequence homology with the relevant portions of the molecules to which they correlate.

Other differences and alterations in the sequence and means for affecting them will be readily apparent to those skilled in the art, and the present invention envisages all of these. The promoters, ferredoxins, and cytochrome P-450 of the present invention which vary in such a way other than by natural variation, are also referred to herein as mutants so that both mutants and variants are envisaged so long as they function together to result in production of a microorganism capable of hydroxylating ML-236B (compactin) to form pravastatin.

If desired, the nucleotide sequence of any cloned DNA can be determined by, for example, the Maxam-Gilbert chemical modification method [Maxam, A. M., and Gilbert, W., (1980), Methods in Enzymology, 65, 499-599] or the dideoxy chain termination method using M13 phage [Messing, J., and Vieira, J., (1982), Gene, 19, 269-276].

Furthermore, it will be appreciated that the terms "expression product", "protein" and "polypeptide" are generally interchangeable, and are used in such a sense herein. In certain circumstances, the polypeptide translated from the original DNA is not the final product, but is an intermediate form of the final product, post-translational modifications being required to obtain the required product. In the case of P-450sca-2, iron needs to be incorporated into a heme ring in the protein to generate the final expression product. Thus, while the terms "expression product", "protein" and "polypeptide" are used synonymously herein, the differences between the terms will be recognized by the person skilled in the art in the relevant context.

Following construction of appropriate expression vector(s) designed to express cytochrome P-450 and ferredoxin or ferredoxin like proteins, said vector(s) are transformed into a suitable host. Preferred hosts include actinomycetes and ascomycota, however, other prokaryotes and eukaryotes, such as, for example, Escherichia coli and, Bacillus subtilis, may also be utilized. In specific embodiments of the invention, Streptomyces lividans TK 21 and Penicillium citrinum are transformed.

Suitable transformation methods for use with an actinomycete comprise forming the actinomycete culture into spheroplasts using lysozyme. A buffer solution containing recombinant DNA vectors and polyethylene glycol is then added, in order to introduce the expression vector into the host cells, by using either of the methods of Thompson or Hopwood [c.f. Thompson, C. J., et al., (1982), J. Bacteriol., 151, 668-677 or Hopwood, D. A., et al., (1985), "Genetic Manipulation of Streptomyces: A Laboratory Manual", The John Innes Foundation, Norwich], for example. In a non-limiting embodiment of the invention, a thiostrepton-resistance gene is used as a selective marker in the expression vector plasmid [c.f. Hopwood, D. A., et al., (1987), "Methods in Enzymology" 153, 116, Academic Press, New York].

If transformation of E. coli is desired, in order to express a product under the control of a promoter of the present invention, then an appropriate general method is one wherein the relevant recombinant DNA vector is added to competent cells. The competent cells are generally prepared in the presence of salts such as calcium chloride, magnesium chloride and rubidium chloride [c.f. Hanahan, D., (1983), J. Mol. Biol. 166, 557-580]. An alternative method comprises electroporation, which involves the use of high-voltage pulses applied to a suspension comprising the host E. Coli and the expression vector, thereby causing incorporation of the vector into the cells [Electroporation: Dower, W. J., et al., (1988), Nucleic Acid Res., 16, 6127 and Calvin, N. M., et al., (1988), J. Bacteriol., 170, 2796].

In the event that B. subtilis is intended as the host cell, then a suitable method is one wherein the host cells are made into protoplasts using lysozyme. A buffer solution containing recombinant DNA vectors and polyethylene glycol is then added to the protoplasts, followed by incorporation of the vector into the host cells by electroporation (supra) [Cheng, S., et al., (1979), Mol. Gen. Genet., 168, 111]. In a preferred embodiment, a drug-resistance marker, such as that for chloramphenicol resistance, is used as a selective marker for the transformed cell line, but it will be appreciated that many other selective markers may be used.

Regardless of the host, the desired transformant can be cultured using methods well known to those skilled in the art, with the desired polypeptide(s) being produced by the culture either intracellularly or extracellularly, or both. Media that are used in the culture can be suitably selected from various types of media commonly used for the relevant host cells. In general, those culture conditions, which are accepted as normal for the particular host can also be used for the expression of the desired polypeptide, subject to any modifications required by the properties of the polypeptide, for example. Additionally, should the expression vector contain an inducible promoter, it may be necessary to add compounds capable of inducing expression of the cloned genes.

The particular cultivation technique employed is not critical to the invention and any technique commonly used for cultivation may equally be employed for the present invention. In general, the techniques employed will be chosen having regard to industrial efficiency. Typical actinomycete nutrients, for use as source of assimilable carbon include glucose, sucrose, starch, glycerol, starch syrup, molasses and soybean oil for use as the carbon source. Examples of sources of assimilable nitrogen include soybean powder, wheat germ, meat extract, peptone, corn steep liquor, dry yeast and ammonium sulfate. In addition to the above, inorganic salts such as sodium chloride, potassium chloride, calcium carbonate or phosphate, and additives for assisting the growth of the micro-organism or promoting production of the desired polypeptide can also be suitably used in combination as necessary.

Again, culture techniques generally appropriate to the host in question are also applicable to the transformed microorganisms, including such methods as liquid culturing and deep culturing, suitable for production on an industrial scale. Culture conditions, unless otherwise generally contra-indicated, or specified herein, involve temperatures of between 20° C. and 37° C., preferably between 26° C. and 28° C. The expression product, i.e., cytochrome P-450 and ferredoxin or a ferredoxin like protein, under the control of a promoter of the present invention is generally produced intracellularly or extracellularly, and occasionally both.

In yet another embodiment of the invention, the cytochrome P-450 and ferredoxin can be isolated, purified and recovered by various procedures, such as are well known to those skilled in the art, particularly those procedures relying upon the physical or chemical properties of the polypeptide. In the case where the polypeptides are expressed externally, the polypeptides can be isolated, purified and recovered from the resulting supernatant by centrifuging the culture medium, for example, to remove cells.

In order to isolate and purify cytochrome P-450 and ferredoxin proteins which have accumulated inside the cells, the cells are first suspended in a solution containing a protease inhibitor and then homogenized using a means, such as one commonly known to those skilled in the art such as, for example, an ultrasonic homogenizer.

Although it is not generally necessary for the elucidation of the present invention, it will be appreciated that examples of specific methods for the isolation, purification and collection of the desired polypeptides include such techniques as protein precipitation, ultrafiltration, molecular sieve chromatography (gel filtration), adsorption chromatography, ion exchange chromatography, affinity chromatography, the various appropriate types of liquid chromatography, including high-performance liquid chromatography (HPLC), dialysis and combinations thereof.

In any event, it will be appreciated that the desired polypeptides can easily be produced on an industrial scale, both in high yield and in high purity, using the present invention. It will also be appreciated that it is possible to utilize the cytochrome P-450 and ferredoxin or ferredoxin like protein produced by transformed host cells of the present invention using an unpurified, or partially purified, preparation sample. Cytochrome P-450 and ferredoxin or ferredoxin like protein can be obtained from the recombinant *Streptomyces lividans* in a manner as described above, and used directly in the production of pravastatin, for example Pravastatin produced by any of the processes of the present invention can be recovered by the method of Serizawa, et al. [c.f. Serizawa, N., et al., (1983), J. Antibiotics, 36, 608]. In a specific embodiment, *Streptomyces lividans* TK-21 may be used in such a manner.

This invention further provides a pharmaceutical composition comprising pravastatin or fragment thereof, prepared using the methods and compositions of the present invention, and a pharmaceutically acceptable carrier.

Carrier, as used herein, include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt forming counterions such as sodium; and/or nonionic surfactants such as TWEEN®, polyethylene glycol (PEG), and PLURONICS®.

The active ingredients may also be entrapped in microcapsules prepared, for example, by interfacial polymerization, for example, hydroxymethylcellulose or gelatin-microcapsules and poly(methylmethacylate) microcapsules, respectively, in colloidal drug delivery systems (for example, liposomes, albumin microspheres, microemulsions, nanoparticles, and nanocapsules) or in macroemulsions. The formulations to be used for in vivo administration must be sterile. This is readily accomplished by filtration through sterile filtration membranes. Sustained-release preparations maybe prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

Treatment means any treatment of a disease in an animal and includes: (1) preventing the disease from occurring in a mammal which may be predisposed to the disease but does not yet experience or display symptoms of the disease; e.g., prevention of the outbreak of the clinical symptoms; (2) inhibiting the disease, e.g., arresting its development; or (3) relieving the disease, e.g., causing regression of the symptoms of the disease.

In a specific embodiment of the invention, the pravastatin prepared using the methods and compositions of the present invention are used to treat disorders relating to cholesterol biosynthesis. Such disorders include but are not limited to hypercholesterolemia and hyperlipidemia.

Effective amount for the treatment of a disease means that amount which, when administered to a mammal in need thereof, is sufficient to effect treatment, as defined above, for that disease.

In any event, it will be appreciated that the desired pravastatin can be easily produced on an industrial scale, both in high yield and in high purity, using the present invention.

Having described the invention with reference to certain preferred embodiments, other embodiments will become apparent to one skilled in the art from consideration of the specification. Any methods, preparations, solutions and such like, which are not specifically defined, may be found in "Molecular Cloning—A Laboratory Handbook" (supra) which is hereby incorporated in its entirety by this reference. The invention is further defined by reference to the following examples describing in detail the preparation of the compound of the present invention. It will be apparent to those skilled in the art that many modifications, both to materials and methods, may be practiced without departing from the scope of the invention.

EXAMPLES

Example 1

Comparative Example

This example illustrates that, transforming the cytochrome P450 gene into *S. lividans* TK-21 without the fdxshe or fdxshe-like gene is not sufficient to induce hydroxylation of compactin to pravastatin.

Construction of pWHM-CytP450she Plasmid:

Total DNA was extracted from *S. helvaticus* using PURE-GENE DNA isolation Kit modified for Yeast and Gram-positive Bacteria. The cytP450she gene was PCR amplified using synthetic oligonucleotide primers 5' TAT AAG CTT TGC GGT AGA CCG CCG CCT TTC 3' (SEQ ID NO: 4) and 5' TTT CTA GAC CAG GTG ACC GGG AGT TCG TTG 3' (SEQ ID NO: 5 based on Genbank sequences: E06907 and E13579. The PCR fragment was purified from the PCR mix (V-gene PCR Purification Kit) and digested with HindIII and EcoRI restriction enzymes at 37°C. for 2 hours using buffers and enzymes recommended by the producer (MBI Fermentas).

The product of the digestion reaction were separated by agarose gel electrophoresis on a 1% w/v agarose gel in a submarine-type electrophoresis tank containing TAE solution and run at 100 V for 3 hours. The agarose slice containing the relevant 1.2 kb fragment was excised from the gel and the DNA was extracted from the gel using V-gene DNA Gel Extraction Kit. The purified and digested PCR fragment was ligated into the PWHM-3 (Vara et al, 1989) vector (cut with HindIII and EcoRI, and purified similar to the PCR fragment purification).

The ligation mix was electroporated into *E. coli* XL1-blue cells using BIO-RAD MicroPulser Electroporation Apparatus and plated on ampicillin containing LB medium. Ampicillin resistant colonies were isolated and grown overnight in LB medium containing 100 ug/ml ampicillin. From the overnight cultures, plasmid DNA was extracted using the V-gene Rapid Plasmid DNA Daily Mini-prep Kit. Extracted plasmid DNA was digested with EcoRI and HindIII and run on 1% agarose gel in TAE buffer. Plasmid construct containing the desired sized insert were selected and sequenced and used in subsequent works (pWHM-CytP450she).

Transformation of the pWHM-CytP450she Construct into *S. lividans* TK-21:

The plasmid construct was transformed into *S. lividans* TK-21 protoplasts as described in Hopwood (1985) and selected on thiostreptone containing R2YE medium. Thiostreptone resistant colonies were transferred to separate thiostreptone containing R2YE petri-dishes and allowed to sporulate at 28° C. Spores were washed separately from each petri-dish in 10% glycerol and stored at −20° C. until use. From each, 0.5 mL spore suspension were used to inoculate 100 mL YEME medium (Hopwood et al, 1985) containing 25 µg/g thiostreptone and allowed to grow for 3 days.

Plasmid DNA was purified and digested with EcoRI and HindIII and separated on agarose gels. All tested plasmid construct showed the expected restriction pattern. One of the tested spore suspension was selected and used in subsequent work.

Testing the Compactin Hydroxylation of *S. lividans* TK-21 Carrying the pWHM-cytP450she Construct:

Previously selected spore suspension was used to inoculate 50 mL PSI medium (2% glucose, 0.5% soybean meal, 0.5% soy-peptone, 0.01% $KH_2PO_4$ and 0.1% $CaCO_3$) and incubated for 2 days with continuous orbital shaking with 300 rpm at 28° C. This preculture was used to inoculate the 50 mL PSF-2 medium (1.8% glucose, 5% soybean meal, 0.4% CSL and 0.3% $CaCO_3$ pH=7.2) using 10% of inoculum. The culture was grown for 30-40 hours and 1 mL 40 mg/ml compactin-Na solution was added to the fermentation. Fermentation was left to run for another 24-48 hours. Samples were then collected and were analyzed by high-performance liquid chromatography. The pravastatin production was 0-3 µg/g.

Example 2

This example illustrates that, transforming the cytochrome P450 gene into *S. lividans* TK-21 with the fdxshe or fdxshe-like gene is sufficient to induce hydroxylation of compactin to pravastatin.

Isolation of fdxshe Gene by Inverse PCR:

Total DNA was extracted from *S. helvaticus* using PURE-GENE DNA isolation Kit modified for Yeast and Gram-positive Bacteria. The genomic DNA was digested with BamHI, diluted to ten-fold, and self-ligated. Using the ligation mix PCR was done using the primers: 5'CGA ACT CCC GGT CAC CTG GTG ACC G 3' (SEQ ID NO: 6) and 5' GTC ATG CGG CGA CGC GTC CCG TGC L 3' (SEQ ID NO: 7). PCR products were separated on 0.7% agarose gel and a single PCR product was seen. The PCR product was sequenced: See FIG. 1 (SEQ ID NO: 1).

An ORF was identified downstream from the cytP450she gene, which showed 70% identity to the *S. griseolus* ferredoxin-1 (suaB) gene, and it was called fdxshe.

Construction of the pWHM-cytP450she-fdxshe Construct:

Based on the sequence information a new primer was designed and positioned downstream of the fdxshe stop codon. Using the 5' TAT AAG CTT TGC GGT AGA CCG CCG CCT TTC 3' (SEQ ID NO: 4) and the newly designed 5' AAA GAA TTC GTG ACC GAT CCG CTG TGA CGC C 3' (SEQ ID NO: 8) primers, the cytP450she and the newly identified fdxshe was amplified together from the S. helvaticus genomic DNA. The desired sized PCR fragment was cloned into a pWHM-3 vector as in Example 1.

Transformation of the pWHM-CytP450she-fdxshe Construct into S. lividans TK-21:

The plasmid construct was transformed in S. lividans TK-21 in the same way as it was described in Example 1. Spores were prepared and the desired sized inserts were selected in the same way as it was done in Example 1.

Testing the Compactin Hydroxylation of S. lividans TK-21 Carrying the pWHM-cytP450she-fdxshe Construct:

The previously selected spore suspension was used to inoculate PSI and PSF-2 medium. The fermentation was done as described in Example 1. The pravastatin production of S. lividans colonies carrying the pWHM-cytP450she-fdxshe plasmid was 478-502 µg/g.

Example 3

This example illustrates that, transforming the cytochrome P450 gene into S. lividans TK-21 with the fdxshe or fdxshe-like gene is sufficient to induce hydroxylation of compactin to pravastatin.

Transformation of the pWHM-CytP450she-fdxshe Construct into S. helvaticus:

The pWHM-CytP450she-fdxshe plasmid construct (described in example 2) was transformed into protoplasts of S. helvaticus by electroporation. Protoplasts were prepared as described by Bibb et al, 1978, except cells were grown in ISP-2 medium instead of YEME for 48 h at 28° C. Protoplasts were washed into 10% sucrose solution before electroporation. Electroporation was done in a 2 mm gap electroporation chamber (BIO-RAD) with the following parameter settings: 1.5 kV, 600Ω and 10 µF on a Bio-Rad MicroPulser Electroporation Apparatus. Transformed protoplasts were regenerated on ISP-2 medium+10% sucrose for 24 hours at 28° C. and than overlayed with 5 ml SNA medium containing 15 µl of 50 mg/ml thiostreptone solution. After the solidification of the agar overlay the incubation was continued at 28° C. Regenerated transformant colonies appeared after 5-7 days. Growing colonies were transferred to IPS-2 medium+25 µg/ml thiostreptone and grown for another 5-7 days. Still growing colonies were used in the subsequent steps. Selected colonies were grown in ISP-2 medium+25 µg/ml thiostreptone and plasmid DNA was purified from the mycelia and tested by restriction digestion. The isolated plasmid DNAs showed similar restriction pattern with the original pWHM-CytP450she-fdxshe construct.

Testing the Compactin Hydroxylation of S. helvaticus Carrying the pWHM-cytP450she-fdxshe Construct:

Two previously selected colonies were used to inoculate PSI and PSF-2 medium. The fermentation was done as described in Example 1. The pravastatin production rate of the S. helvaticus colonies carrying the pWHM-cytP450she-fdxshe plasmid was 212-263 µg/g/2 h compared to the original strains which did not carried the cytP450sca-fdxshe construct, where the pravastatin production was only 114-116 µg/g/2 h.

Example 4

From the start codon (ATG) to the stop codon (TGA) the CytP450she ORF is PCR amplified and cloned between the pgk promoter and trpc terminator into the MCS of the pBC-Hygro vector (Silar, FGN 42:73). From the start codon (ATG) to the stop codon (TGA) the fdxshe ORF is PCR amplified and cloned between pgk promoter and trpC terminator into the MCS of the pBC-Phleo vector (Silar, FGN 42:73). Constructs are tested by restriction enzyme digestion and suitable clones showing the expected fragment sizes are further tested by sequencing. Clones with the expected DNA sequence are selected and used in the subsequent steps.

Both constructs are transformed sequentially into Penicillium citrinum protoplasts, selecting on 200 ug/ml hygromycin and 500 ug/ml phleomycin respectively. Isolates showing both hygromycin and phleomycin resistance are selected and tested for compactin to pravastatin conversion after one dose compactin-Na feeding. Isolates able to convert compactin to pravastatin are further tested.

What is claimed is:

1. An isolated nucleic acid molecule comprising the nucleotide sequence of SEQ ID NO: 1.

2. An isolated nucleic acid molecule having at least 90% sequence identity to SEQ ID NO: 1 and encoding a polypeptide having compactin hydroxylase or ferredoxin reductase activity.

3. The isolated nucleic acid molecule of claim 2 having at least 95% sequence identity to SEQ ID NO: 1.

4. An isolated nucleic acid molecule that is the full length complement of the nucleic acid molecule of any one of claims 1, 2 and 3.

5. An isolated nucleic acid molecule that hybridizes to SEQ ID NO: 1 under the following stringent conditions: hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C., wherein said nucleic acid molecule encodes a polypeptide having compactin hydroxylase or ferredoxin reductase activity.

6. A vector comprising a polynucleotide according to any one of claims 1, 2 and 3.

7. An isolated host cell comprising the vector of claim 6.

8. A method for producing an isolated polypeptide comprising culturing the isolated host cell of claim 7 under in vitro conditions in which the protein encoded by the nucleic acid molecule is expressed; and recovering the protein from the culture.

9. An isolated nucleic acid molecule encoding the polypeptide molecule of SEQ ID NO: 2.

\* \* \* \* \*

SEQUENCE LISTING

<160> NUMBER OF SEQ ID NOS: 8

<210> SEQ ID NO 1
<211> LENGTH: 230
<212> TYPE: DNA
<213> ORGANISM: Streptomyces lividans
<220> FEATURE:
<221> NAME/KEY: misc_feature
<222> LOCATION: (213)..(213)
<223> OTHER INFORMATION: n is a, c, g or t

<400> SEQUENCE: 1

```
ccgagcggaa aggaggaccc atgcgggtct cagcggaccg ggacgtctgt gtcggcgccg      60
gcctgtgcgc gctgaccgcg cccgacgtct ttgaccagga cgacgacggc cttgttgacg     120
tggtcacccc cgatcccggc caggcgcagc aggccgcggc ccgccaggcc ggcaacctct     180
```

-continued

```
gtccgtcggg ggcggtccgc atcaccgaat gangcgaccg tcccgcggcc              230
```

<210> SEQ ID NO 2
<211> LENGTH: 63
<212> TYPE: PRT
<213> ORGANISM: Streptomyces lividans

<400> SEQUENCE: 2

```
Met Arg Val Ser Ala Asp Arg Asp Val Cys Val Gly Ala Gly Leu Cys
1               5                   10                  15

Ala Leu Thr Ala Pro Asp Val Phe Asp Gln Asp Asp Gly Leu Val
            20                  25                  30

Asp Val Val Thr Pro Asp Pro Gly Gln Ala Gln Gln Ala Ala Ala Arg
        35                  40                  45

Gln Ala Gly Asn Leu Cys Pro Ser Gly Ala Val Arg Ile Thr Glu
    50                  55                  60
```

<210> SEQ ID NO 3
<211> LENGTH: 230
<212> TYPE: DNA
<213> ORGANISM: Streptomyces lividans
<220> FEATURE:
<221> NAME/KEY: misc_feature
<222> LOCATION: (213)..(213)
<223> OTHER INFORMATION: n is a, c, g or t

<400> SEQUENCE: 3

```
ggctcgcctt tcctcctggg tacgcccaga gtcgcctggc cctgcagaca cagccgcggc      60
cggacacgcg cgactggcgc gggctgcaga aactggtcct gctgctgccg gaacaactgc     120
accagtgggg gctagggccg gtccgcgtcg tccggcgccg gcggtccgg ccgttggaga      180 caggcagccc ccgccaggcg tagtggctta ctncgctggc agggcgccgg                230
```

<210> SEQ ID NO 4
<211> LENGTH: 30
<212> TYPE: DNA
<213> ORGANISM: Artificial Sequence
<220> FEATURE:
<223> OTHER INFORMATION: chemically synthesized PCR primer

<400> SEQUENCE: 4

```
tataagcttt gcggtagacc gccgcctttc                                      30
```

<210> SEQ ID NO 5
<211> LENGTH: 30
<212> TYPE: DNA
<213> ORGANISM: Artificial Sequence
<220> FEATURE:
<223> OTHER INFORMATION: chemically synthesized PCR primer

<400> SEQUENCE: 5

```
tttctagacc aggtgaccgg gagttcgttg                                      30
```

<210> SEQ ID NO 6
<211> LENGTH: 25
<212> TYPE: DNA
<213> ORGANISM: Artificial Sequence
<220> FEATURE:
<223> OTHER INFORMATION: chemically synthesized PCR primer

<400> SEQUENCE: 6

```
cgaactcccg gtcacctggt gaccg                                           25
```

```
<210> SEQ ID NO 7
<211> LENGTH: 25
<212> TYPE: DNA
<213> ORGANISM: Artificial Sequence
<220> FEATURE:
<223> OTHER INFORMATION: chemically synthesiszed PCR primer

<400> SEQUENCE: 7
gtcatgcggc gacgcgtccc gtgct                                              25

<210> SEQ ID NO 8
<211> LENGTH: 31
<212> TYPE: DNA
<213> ORGANISM: Artificial Sequence
<220> FEATURE:
<223> OTHER INFORMATION: chemically synthesized PCR primer

<400> SEQUENCE: 8
aaagaattcg tgaccgatcc gctgtgacgc c                                       31
```